United States Patent [19]

Kung et al.

[11] Patent Number: 4,978,608
[45] Date of Patent: Dec. 18, 1990

[54] DNA DETECTION SYSTEM

[75] Inventors: Viola T. Kung, Menlo Park; Peter A. Nagainis, San Jose, both of Calif.

[73] Assignee: Molecular Devices Corporation, Palo Alto, Calif.

[21] Appl. No.: 93,361

[22] Filed: Sep. 4, 1987

[51] Int. Cl.$^5$ .................... G01N 33/53; G01N 33/00; G01N 33/566; C12Q 1/68
[52] U.S. Cl. ......................................... 435/6; 435/7; 436/501; 436/94; 935/77
[58] Field of Search .................. 435/6, 7; 935/77, 78; 436/94, 501

[56] References Cited

U.S. PATENT DOCUMENTS 4,493,899  1/1985  Smith .
4,493,899  1/1985  Smith et al. .

FOREIGN PATENT DOCUMENTS 0135159    8/1984   European Pat. Off. .
0147665A1  11/1984  European Pat. Off. .
0131830    1/1985   European Pat. Off. .
0212603    4/1987   European Pat. Off. ............ 436/94
WO85/05685 12/1985  PCT Int'l Appl. .
2125964A   7/1983   United Kingdom .

OTHER PUBLICATIONS

Syvanen et al., Nucleic Acid Research, 13, pp. 2789–2802, 1985.
Voller et al., in Manual of Chemical Immunology, 3rd Ed., ASM, Washington, D.C., Editors, Rose, N. R. et al., pp. 99–109, 1986.
Vogelstein et al., Proc. Natl. Acad. Sci. U.S.A., "Preparative and Analytical Purification of DNA from Agarose", 76:615–619, (1979).
Martin Gellert, The Enzymes, "DNA Gyrase and Other Type II Topoisomerases", 14:345–366, (1981).
James C. Wang, The Enzymes, "Type I DNA Topoisomerases", 14:332–434, (1981).
"Deoxyribonucleic Acid Topoisomerase I from Chicken Erythrocytes: Purification, Characterization, and Detection by a DNA Binding Assay," by Tricoli et al., Biochemistry, (1983), 22(8):2025–2031.
"Large-Scale Overproduction and Rapid Purification of the Escherichia coli SSB Gene Product. Expression of the SSB Gene under $\lambda$ $P_L$ Control," by Lohman et al., Biochemistry, (1986), 25:21–25.
Smith et al., 1981, J. Lab. Clin. Med., 98:425–436.
Chase et al., Ann. Biochem., "Single-Stranded DNA Binding Proteins Required for DNA Replication", 55:103–136, (1986).
Kowalczykowski et al., Biochemistry, "DNA Binding Proteins", 17:425–429, (1978).
Krauss et al., Biochemistry, "Escherichia coli Single-Strand Deoxyribonucleic Acid Binding Protein: Stability, Specificity, and Kinetics of Complexes with Oligonucleotides and Deoxyribonucleic Acid", 20:5346–5352, (1981).
Kung et al., The Journal of Biological Chemistry, "Purification and Characterization of an $\omega$ Protein from Micrococcus luteus", 252:5398–5402, (1977).
DuClos et al., Journal of Immunological Methods, "Monoclonal Antibody for DNA Measurement in Biological Fluids", 88:185–192, (1986).

Primary Examiner—Christine Nucker
Assistant Examiner—Karen I. Krupen
Attorney, Agent, or Firm—Allegretti & Witcoff, Ltd.

[57] ABSTRACT

Picogram amounts of DNA can be detected in a sample by the use of high affinity single-stranded DNA binding proteins. The assay is applicable not only to pure DNA samples but also to samples containing significant amounts of protein.

27 Claims, No Drawings

DNA DETECTION SYSTEM

INTRODUCTION

Technical Field

This invention relates to methods for detecting the presence of DNA. The method employs high affinity binding proteins for single stranded DNA.

BACKGROUND

The amount of DNA in a sample has traditionally been measured either by spectrophotometric means or fluorometrically with the use of ethidium bromide. If the sample is pure (does not contain significant amounts of contaminants such as protein, phenol, agarose, or other nucleic acids) the spectrophotometric measurement of the amount of ultraviolet (UV) irradiation absorbed is simple and accurate. However, if there is contamination with protein or compounds which absorb strongly in the UV, such as phenol, accurate quantitation of the amount of DNA will not be possible. Furthermore, this technique is only suitable for samples containing DNA in the µg/ml range.

If the amount of DNA in the sample is small, or if the sample contains significant quantities of impurities, the amount of DNA may be estimated from the intensity of UV-induced fluorescence emitted by ethidium bromide intercalated into the DNA. The amount of fluorescence is proportional to the total amount of DNA. The quantity of DNA in the sample therefore can be estimated by comparing the fluorescent yield of the sample with that of a series of standards. As little as 1 to 5 µg/ml of DNA can be detected by this method. With the use of a minifluorometer (such as that manufactured by Hoefer Scientific Instruments, San Francisco, Calif.) and the fluorochrome Hoechst 33258, the sensitivity may be increased to 10 ng/ml.

With the advent of recombinant DNA technology, it has become imperative to be able to identify significantly lower concentrations of DNA in a sample, for example, any contaminating DNA which may be present in a recombinant product. The contaminating DNA may be non-specific and of unknown sequence. Therefore, enzyme amplification of sample DNA (using for example the DNA polymerase chain reaction method) is difficult for lack of universal primers for DNA synthesis. There is, therefore, substantial interest in being able to detect rapidly and accurately the presence of extremely small amounts of DNA.

Relevant Literature

Krauss et al., *Biochemistry* (1981) 22:5346–5352 disclose the binding of single-stranded binding proteins from *E. coli* to oligonucleotides. Vogelstein and Gillespie, *Proc. Natl Acad. Sci. USA* (1979) 76:615–619 disclose the binding of DNA to glass. Kung et al. disclose the purification of topoisomerase I from *Micrococcus luteus* by high salt elution from a DNA-sepharose column *J. Biol. Chem.* (1977) 252:5398–5402 The following are review articles pertaining to DNA binding proteins. Gellert, *The Enzymes*, Vol. XIV (1981) 345–366 Wang, *The Enzymes*, Vol. XIV (1981) 332–343: Chase, *Ann. Rev. Biochem.* (1986) 55:103–136 Kowalczykowski et al., *The Enzymes*, Vol. XIV (1981) 375–444.

SUMMARY OF THE INVENTION

Novel methods are provided employing DNA binding proteins which have high affinity for single-stranded DNA for detecting the presence of DNA in a sample. To detect the presence of DNA, a sample, optionally pretreated, is denatured and any single-stranded DNA (ssDNA) is non-diffusively bound to a solid support where the ssDNA is brought into contact with a single-stranded binding protein (BP) which is either bound non-diffusively to the solid support, or added in soluble form. The ssDNA binds to the BP forming ssDNABP complexes which may be detected by means of a label on either the BP or the ssDNA, depending upon the protocol used.

DESCRIPTION OF THE SPECIFIC EMBODIMENTS

In accordance with the subject invention, methods and compositions are provided for determining the presence of DNA in a sample, particularly in a protein product produced in culture, e.g., fermentation. The presence of DNA may be detected by the use of high affinity, single-stranded DNA binding proteins.

The single-stranded DNA binding protein may be from any source, either eukaryotic or prokaryotic, and may include single-stranded DNA binding proteins, topoisomerases, and DNA unwinding proteins. Of particular interest are single-stranded DNA binding protein from *E. coli*, T4 gene 32 protein and topoisomerase I from *Micrococcus luteus* and *E. coli*.

The DNA binding protein is characterized as having high affinity for single-stranded DNA (ssDNA), at least $10^5 M^{-1}$, usually in the range of about $10-10^{10} M^{-1}$ when the ssDNA is at least 100 nucleotides long. Alternatively, the protein may be characterized as a single-stranded DNA binding protein requiring a concentration of greater than about 0.4M sodium chloride (or other monovalent salt providing comparable ionic strength) for elution from ssDNA-cellulose or ssDNA-sepharose. Generally the concentration for elution is greater than about 0.6M sodium chloride, and preferably greater than about 1.0M sodium chloride. When determining the affinity, an aqueous buffer, pH 6 to 9 at 25° C. should be used. No detergent, denaturant (for example, urea, guanidium chloride), chaotropic agent or organic solvent should be present in the buffer.

The single-stranded DNA binding protein can be used unbound to any other component, and/or it can be non-diffusively bound, covalently or adsorptively, to a solid support or covalently to a label.

Various solid support materials may be employed with conventional procedures used for non-diffusive binding of the single-stranded DNA binding protein (BP), as appropriate. The solid support may include filter membranes, preferably Immobilon ™ or nitrocellulose. The pore size of the nitrocellulose membrane may be less than 5µ, preferably less than 1µ; and is usually greater than 0.05µ, preferably greater than 0.1µ. The single-stranded DNA binding protein may be non-diffusively bound to the filter membrane by any conventional means, including covalent binding to carbonyl imidazole groups, or other active groups present on the membrane, or non-covalently by absorption to the membrane.

The solid support may be chromatographic bed materials, monodisperse latex particles, including those based on styrene, chemically-modified styrene, propylene, methacrylate, butadiene, acrylonitrile or other monomers; polyglutaraldehyde microspheres (e.g., as manufactured by Polysciences, Inc.), nylon beads, chemically-modified nylon beads, oxirane acrylic beads such as Eupergit ® (Rohm Pharma, Darmstadt, W. Germany): copolymers of acrylic ester and acrylic amide. Single-stranded DNA binding protein may be covalently bound to an activated chromatographic resin having reactive groups capable of forming covalent bonds with proteins, such as CNBr-activated Sepharose-4B, CNBr-activated 4% Agarose or CNBr-activated Sepharose-6MB (Pharmacia P-L Biochemicals: Piscataway, N.J.), or other resin, such as cellulose, by conventional means. Single-stranded DNA binding protein may be bound to polystyrene beads by non-specific adsorption. Single-stranded binding protein may also be bound covalently to polystyrene beads containing carboxyl or amino functional groups (Polysciences, Inc. Warrington, Pa.) by conventional means.

The DNA, generally denatured to single-stranded DNA (ssDNA), can be bound non-diffusively to a solid support, either absorptively or covalently. The solid support can be a membrane such as nitrocellulose. The sample containing the ssDNA is filtered onto the membrane. The salt concentration of the sample is greater than 50 mM sodium chloride, preferably greater than 100 mM sodium chloride, or other salt providing similar ionic strength. The ssDNA is then fixed on the membrane by, for example, baking the membrane at between 75° C. and 100° C., preferably at 80° C. for at least 30 minutes, usually for at least 1 hour, and preferably no more than 6 hours. Other methods of fixing the ssDNA on the membrane include washing the membrane with ethanol. The solid support can be positively-charged nylon such as beads or membranes (for example Nytran ® (Schleicher and Schull, Inc. Keene, N.H.), GeneScreen Plus ™ (duPont Company: Boston, Mass.), Zeta-Probe ® (BioRad Labs; Pinole, Calif.), Bio-Trace ™ (Gelman Sciences, Inc. Ann Arbor, Mich.), Bio-dyne B ® (Pall Biosupport Glen Cove, N.Y.), and Genatran ™ (Plasco, Inc. Woburn, Mass.)). The ssDNA can be selectively non-diffusively bound to the positively-charged nylon by incubating the nylon in a buffer at between pH 6 and 9 comprising an appropriate salt concentration and/or non-ionic detergent. The appropriate salt concentration is preferably less than 1M sodium chloride (or other salt providing similar ionic strength), and preferably less than 0.6M sodium chloride. Examples of non-ionic detergents which can be used include Tween-20 ® or Triton X-100 ® at a concentration of 0.1–5.0% v/v.

The sample may be any sample in which it is desired to detect DNA when it is present at a low concentration. The sample may be a solid or a liquid, such as a proteinaceous lyophilized composition or aqueous medium. Samples can include proteins made by recombinant DNA methods, for example, tissue plasminogen activator, insulin, growth hormone, interleukin II, and interferons monoclonal antibodies prepared for therapeutic purposes water for use in procedures requiring absolute purity.

The method for carrying out the subject invention is as follows. If the sample contains protein, the protein is optionally removed. The DNA is then denatured to ssDNA, and the ssDNA bound non-diffusively to a solid support. If the solid support does not contain non-diffusively bound BP, the ssDNA may be fixed on the solid support by for example baking, treatment with ethanol, or other convenient means. BP is then added to the solid support and binds specifically to the ssDNA. When the solid support comprises BP, the ssDNA binds specifically to the BP and the fixing step is omitted. Whether any DNA is present in the sample is determined by detecting ssDNA-BP complexes on the solid support by means of a label on either the BP or the ssDNA.

When it is desired to determine the concentration of DNA present at least one background solution containing no DNA and at least one reference solution containing a known amount of DNA are treated identically to the sample containing an unknown concentration of DNA. The amount of label detectable in the background solution is subtracted from the amount of label detectable in the reference solution and the unknown sample. The adjusted values for the reference solution and the unknown sample are then related to determine the amount of DNA present in the sample.

The following are general methods for carrying out the above steps. The method of the present invention can be used for the detection of DNA in either the presence or absence of protein When protein is present, an additional step to deproteinize the sample is desirable. Any conventional means can be used (for example, phenol extraction) which does not adversely affect the integrity of the DNA. If the protein has known characteristics, the sample may be deproteinized by ion-exchange column chromatography (for example, DEAE-cellulose, phosphocellulose), hydroxyapatite (the single-stranded and double-stranded DNA may be separated from protein by elution with differential salt concentrations), gel filtration, and affinity chromatography Affinity chromatography may be used to remove the protein directly from the sample, e.g., using immobilized mouse immunoglobulin raised against the protein to be removed, or the sample may be deproteinized using immobilized single-stranded DNA binding protein to bind the DNA in the sample which can then be eluted and used in the detection assay.

Generic methods of deproteinization may include mixing the sample with a suspension of glass particles in the presence of a high concentration of sodium iodide whereby DNA present in the sample is non-diffusively bound by the glass particles, isolating the glass particles, and then eluting the DNA with water or phosphate buffered saline (PBS) The glass particles may include finely ground glass beads, or preferably a composition comprising Glassmilk ™ as supplied by BIO 101, Inc., La Jolla, Calif.

Another method which can be used is admixing a protein-containing sample with a proteolytic enzyme composition comprising, for example, at least one of the enzymes pronase or proteinase K. Following the enzymatic treatment, hydrolyzed product is removed, for example, by centrifugation through a membrane with a low molecular weight cutoff (approximately 10,000 or 30,000 as supplied by Centriprep-10, Centriprep-30 Amicon, Danvers, Mass.) or use of a Millipore low-volume ultrafiltration device with a low molecular weight cutoff (approximately 10,000 or 30,000).

After any protein present is digested, removed, or digested plus removed, the DNA is denatured to ssDNA. The methods used include heating at 90°–100° C. or treatment with sodium hydroxide (pH 13.0). After rapid chilling (to prevent the DNA from reannealing) or neutralization (using for example, ammonium acetate or Tris buffer), the ssDNA is contacted with a solid support.

If the solid support is a membrane such as nitrocellulose or positively-charged nylon, the sample is generally filtered using a manifold filtration device However, if the solid support is, for example, positively-charged nylon beads, the beads are incubated in the sample. When the solid support has BP immobilized on its surface, the ssDNA binds to the BP to form BPssDNA complexes. If the solid support does not contain BP, the DNA is fixed on the solid support by baking, or treatment with ethanol This step can be omitted when a positively-charged nylon membrane is used. Non-specific binding sites on nitrocellulose or positively-charged nylon can be blocked by incubation with a high concentration protein solution, such as bovine serum albumin (BSA) or non-fat dry milk solution. For the positively-charged nylon, the non-specific binding sites additionally can be blocked by washing with a non-ionic detergent solution, such as Tween-20® or Triton X-100® usually 0.1–5.0%.

The solid support comprising non-diffusively bound ssDNA is then incubated with labeled BP to form BP-ssDNA complexes. When the solid support is a nitrocellulose or positively-charged nylon membrane, buffer (pH 6–9) containing BP (generally about 0.3 μg/ml) is added to the membrane. The buffer is generally at room temperature and contains sodium chloride, preferably 0.01–0.3M, and in addition, for the positively-charged nylon, contains a non-ionic detergent such as Tween-20® or Triton X-100®, preferably 0.1–5.0% v/v.

Any BP-ssDNA complexes can be detected by means of a label attached to either the BP or the ssDNA, the label generally being attached to the BP except when the BP is pre-attached to the solid support. The BP can be covalently labeled in a number of ways. The label can be an enzyme, for example, alkaline phosphatase, β-D-galactosidase, glucose-6-phosphate dehydrogenase, glucose oxidase, horseradish peroxidase, urease, a radionuclide, such as $^{125}$I; a chemiluminescent or fluorescent compound, such as fluorescein isocyanate: or any other label which provides a detectable signal. BP can be coupled to an enzyme such as urease, which contains at least one free, accessible, non-essential cysteine residue (J. Mol. Catalysis (1984) 23:263–292). Other enzymes which can be coupled in this way include β-D-galactosidase. Alternatively, an enzyme label can be thiolated and then conjugated to the BP. Methods for attaching labels to proteins are described in detail in the scientific literature See for example Healey et al., Clinica Chimica Acta (1983) 134:51–58 Ishikawa et al., J. Immunoassay (1983) 4:209–327 and Tijssen, Practice and Theory of Enzyme Immunoassays (1985) 259–263, Elsevier Science Publishers [Amsterdam].

The DNA to be detected can be labeled, rather than the BP. The label may be a radionuclide, fluorophore or biotin. The label can be introduced to the DNA by any standard enzymatic reaction, such as nick translation, or by terminal labeling, with $^{32}$P, $^{125}$I, or biotin-labeled deoxynucleotide triphosphates (dNTP). The labeled DNA is then denatured to ssDNA by alkali or heat. Alternatively, the DNA can be labeled with a reagent such as isopsoralen which binds to double-stranded DNA. $^{3}$H-isopsoralen or biotin-isopsoralen is available from HRI Research, Inc., Berkeley, Calif. The isopsoralen reagent is bound to DNA by mixing it with a sample, followed by photoirradiation at 340–380 nm. If the label used is isopsoralen, it is unnecessary to denature the labeled DNA, as isopsoralen-labeled DNA is recognized by BP without any denaturing step.

Methods of detection will depend on the type of label used as well as the sensitivity required. When the label is an enzyme, the disappearance of substrate or appearance of reaction product may be measured spectrophotometrically following substrate addition. If the enzyme is, for example, urease, an indicator dye such as cresol red may be used to monitor the change in pH in the sample following addition of enzyme substrate. The change in optical density or the visual intensity of the color change is then correlated with the DNA content of the sample by comparison with identically treated reference solutions containing known concentrations of DNA. Alternatively, any DNA present may be detected by measuring the amount of pH change with a photoresponsive device such as that described in U.S. Pat. No. 4,591,550. Other methods of detecting DNA present in the sample may include quantitating the amount of radioactivity, when the label is a radionuclide. The biotin-label can be detected by, for example, enzyme-labeled avidin, streptavidin or antibiotin.

For convenience, reagents are frequently provided in kits, where the labeled reagent is present in conjunction with buffer, stabilizers, excipients and any additional reagents necessary for the detection of the signal in the performance of the assay.

The following examples are offered by way of illustration and not by way of limitation.

EXPERIMENTAL

EXAMPLE 1

Preparation of BP-Enzyme Conjugates

A. Preparation of BP-Urease Conjugate Using m-maleimidobenzoyl-N-hydroxysuccinimide ester (MBS)

Single-stranded DNA binding protein from E. coli was coupled to the cross-linking agent MBS as follows. One hundred μl of 0.25% MBS in dimethylformamide (DMF) was added to 2.0 ml containing 2 mg of BP in 0.1M phosphate buffer, pH 6.8. The mixture was stirred gently at room temperature for 30 min then separated on a Sephadex G-25. The elution buffer was 0.1M phosphate, pH 6.8. Fractions were monitored by UV absorbance at 280 nm. The first peak eluted from the column contained BP coupled to MBS. The peak fractions (3 ml) were combined with 4 ml of urease (20 mg) in 0.1M phosphate buffer, pH 6.8. The mixture was stirred for 20 min at room temperature. The reaction was then stopped by the addition of 1.75 ml of 500 mM sodium sulfite, in 0.1M sodium phosphate buffer, pH 6.8, containing 10 mM dithiothreitol (DTT). The conjugate formed was separated from unconjugated enzyme by gel filtration chromatography. The purified enzyme conjugate was then diluted 1:1 (v/v) with glycerol. BSA was added to 0.25% (w/v). The conjugate was stored at 2°–8° C.

B. Preparation of BP-Horseradish Peroxidase (HRP) Conjugate Using m-maleimidobenzoyl-N-hydroxysuccinimide ester (MBS)

HRP (Boeringer-Mannheim, La Jolla, Calif.) was thiolated with N-succinimidyl 3-(2-pyridyldithio)propionate (SPDP) (Pierce, Rockville, Ill. by combining 16 mg HRP in 0.1M potassium phosphate buffer, 0.2M sodium chloride, pH 7.5 with 435 μg SPDP in 25 μl dimethylformamide (DMF), and allowing coupling to take place for 30 min at room temperature. Unreacted SPDP was removed by chromatography on Sephadex G-25, eluted with 0.1M potassium phosphate buffer containing 0.2M sodium chloride, pH 7.0.

Dithiopyridine groups on HRP were deblocked by adding 25 mM DTT for 30 min then removing the DTT and the 2-thiopyridine formed by G-25 separation in PBS.

Maleimido-BP was formed by adding 25 µl of a 0.25% solution of MBS in DMF to 1.1 mg of BP in 0.5 ml of 0.1M sodium phosphate buffer, and stirring for 30 min at room temperature. Maleimido-BP was purified on Sephadex G-25 and diluted with PBS. Maleimido-BP was condensed with 15 mg of thiolated HRP by combining the two solutions and reacting for 20 min at room temperature. The reaction was stopped by addition of 12.5 µl of 100 mM 2-mercaptoethanol. The BP-HRP conjugate was made 10% in glycerol and stored at 4° C.

EXAMPLE 2

Detection of Pure DNA in a Sample

A. Visual Determination

Samples containing pure calf thymus DNA (Sigma Chemical Co., St. Louis, Mo.) from 0–100 pg/sample (in 10 mM sodium phosphate, pH 7.0, 0.15M sodium chloride, 1 mM EDTA) were denatured to single-stranded DNA by heating at 100° C. for 10 min followed by rapid chilling. The denatured samples were filtered through 0.45µ nitrocellulose membrane (Schleicher and Schuell; Keene, N.H.) using a manifold filtration device. The membranes were then baked at 80° C. for 1 hour to fix the DNA. BP-urease conjugate, diluted to 0.3 µg/ml in 2% bovine serum albumin (BSA), 2% Ficoll, 2% polyvinylpyrrolidone, 10 mM sodium phosphate, 40 mM sodium chloride, 2 mM EDTA, pH 7.5 was added to the membrane. The membrane was incubated with the BP-urease conjugate for 1 hour at room temperature in a Petri dish in a sufficient volume of conjugate to cover the membrane. The membrane was then washed three times with 0.15M sodium chloride, 1 mM EDTA (pH 6) to remove any non-specifically bound conjugate. Any DNA present was then detected by the addition of enzyme substrate (100 mM urea, 0.15M sodium chloride, 1 mM sodium phosphate, pH 6, 0.5 mM cresol red). The change in pH due to the urease reaction resulted in a color change of the cresol red from orange to purple-red. The visual intensity of the purple-red spot was then correlated with the DNA content of the sample by determining the relative size of the colored spots on the membrane and the intensity of the color.

TABLE 1

| Pure DNA (pg/sample) | Intensity of Color at 3 min |
|---|---|
| 0 | − |
| 10 | + |
| 20 | ++ |
| 50 | +++ |
| 100 | ++++ |

B. Biosensor pH determination

Any DNA present on membranes prepared as described above can also be detected, by measuring the amount of pH change following addition of enzyme substrate, using a photoresponsive device (see for example U.S. Pat. No. 4,591,550). An enzyme substrate mixture containing 1 mM sodium phosphate, 0.01% Tween-20, 100 mM urea, pH 6 was added to the membranes. The change in pH due to the urease reaction resulted in a change in the signal of the photoresponsive device. The change in the signal (in µvolt/sec) was then correlated with the DNA content of the sample.

TABLE 2

| DNA (pg/sample) | µvolt/sec |
|---|---|
| 0 | 64 |
| 12 | 107 |
| 25 | 153 |
| 50 | 268 |
| 100 | 341 |

EXAMPLE 3

A. Immobilization of BP on an Immobilon TM Membrane

Immobilon TM membrane contains carbonyl imidazole groups which bind to epsilon amino groups on lysine or arginine. BP was immobilized on a 0.65µ Immobilon TM membrane (Millipore Bedford, Mass.) by soaking the membrane in phosphate buffered saline containing 0.2 mg/ml BP at room temperature for 1 hour (10 cc protein solution/100 cm$^2$ membrane). The BP solution was removed by decanting. Any remaining active carbonyl imidazole groups on the membrane were quenched with 0.1M ethanolamine (pH 9.5) at room temperature overnight. The membrane was then washed successively in phosphate buffered saline, distilled water, and polyvinylalcohol (15 min each wash), and then dried at 65° C. for 5 min. The dried membrane was then ready for use in the detection system. Four hundred µl of a sample containing single-stranded $^{32}$P-labeled DNA (from 10–1000 pg) in a 10 mg/ml BSA aqueous solution was filtered through the BP-Immobilon TM membrane (filtration time of 10 min). Seventy percent of the $^{32}$P counts were captured on the membrane when the BP concentration was 0.2 mg/ml. Increasing the BP concentration used in the immobilization procedure to 1 mg/ml improved the DNA capture to 80%.

B. Immobilization of BP on Nitrocellulose Membranes

BP was adsorbed to a nitrocellulose membrane (0.45µ pore size, Schleicher and Schuell) by soaking the membrane in phosphate buffered saline containing 50 µg/ml BP at 4° C. overnight. Non-specific binding sites on the membrane were blocked with 10 mg/ml BSA at room temperature for 1 hour. When 400 µl of samples containing 10 mg/ml BSA and $^{32}$P-labeled single-stranded DNA were filtered through the membrane, 36% of the $^{32}$P counts were captured on the nitrocellulose membrane.

EXAMPLE 4

Detection of DNA in Samples Containing Protein

A. Protein removal by glass beads

Four hundred µl of sodium iodide (6M) were added to 200 µl of samples, each containing 2 mg of BSA and 100, 50, 25, or 0 pg calf thymus DNA. Two µl of Glassmilk TM were added and the mixture incubated for 10 min at room temperature. The Glassmilk TM /DNA complex was pelleted by centrifugation for 10 sec in a microcentrifuge. The pellet was washed with 150 µl 20 mM Tris buffer, containing 200 mM sodium chloride, 2 mM EDTA in 55% methanol. The wash procedure was repeated once. After the DNA was eluted with 400 µl phosphate buffered saline, each sample was heated at 100° C. for 10 min to denature the DNA then rapidly chilled. The sample was filtered onto nitrocellulose membranes. DNA was detected using the visual determination procedure described in Example 2.A.

TABLE 4

| DNA (pg/sample) | Intensity of Color at 3 min |
|---|---|
| 0 | slight positive |
| 25 | ++ |
| 50 | +++ |
| 100 | ++++ |

B. Proteinase digestion of protein

Proteinase K and dithiothreitol were added (final concentration 100 μg/ml and 50 mM, respectively) to 100 μl of samples each containing 1 mg BSA and 100, 50, 25, 12, or 0 pg of DNA in phosphate buffered saline. The mixture was incubated at 55° C. for 2 hours to digest the protein. After digestion, all samples were heated at 100° C. for 5 min to inactivate proteinase K and denature DNA to single-stranded DNA. Control samples containing a matching amount of DNA but no protein were denatured at the same time. Each sample, after rapid chilling to prevent reannealing of the DNA, was filtered through a nitrocellulose membrane. Visual determination procedures were carried out as described in Example 2.A to detect the presence of DNA.

TABLE 5

| | Intensity | |
|---|---|---|
| DNA (pg/sample) | With Protein | Without Protein |
| 0 | − | − |
| 12 | + | + |
| 25 | ++ | ++ |
| 50 | +++ | +++ |
| 100 | ++++ | ++++ |

The subject methods and compositions provide a rapid and simple means for detecting picogram amounts of DNA in a sample by the use of high affinity single-stranded DNA binding proteins. The assay is applicable not only to pure DNA samples but may also be used with samples which contain a significant amount of protein.

All publications and patent applications mentioned in this specification are indicative of the level of skill of those skilled in the art to which this invention pertains All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for quantitatively detecting DNA in a sample wherein any DNA to be detected is labelled with a detectable label, said method comprising:
    contacting a solid support with a high affinity single-stranded DNA binding protein (BP) to form immobilized BP;
    contacting any single-stranded DNA in said sample with said immobilized BP to form DNA-BP complexes;
    detecting any DNA-BP complexes by means of said label wherein any DNA-BP complexes detected are indicative of the presence of DNA in said sample.

2. A method according to claim 1, wherein said sample is subjected to DNA denaturing conditions prior to said contacting.

3. A method for quantitatively detecting DNA in a sample using a high affinity single-stranded DNA binding protein (BP), wherein said BP is labelled with a detectable label, said method comprising:
    denaturing any DNA present in said sample;
    binding any denatured DNA non-diffusively to a solid support;
    contacting said solid support with BP to form DNA-BP complexes;
    freeing said solid support of any unbound sample and BP; and
    detecting said complexes by means of said label wherein any DNA-BP complexes detected are indicative of the presence of DNA in said sample.

4. A method according to claim 3, wherein said solid support is a positively charged nylon membrane or a nitrocellulose membrane.

5. A method for quantitatively detecting DNA in a sample, said method comprising:
    contacting a solid support with a high affinity single-stranded DNA binding protein (BP) to form immobilized BP;
    admixing said sample with a photoreactive compound labelled with a detectable label to form a mixture;
    irradiating said mixture with activating light to react said photoreactive compound with any DNA present in said sample;
    contacting said mixture with said immobilized BP to form DNA-BP complexes;
    freeing said solid support of any mixture not specifically bound; and
    detecting any photoreactive compound present on said solid support by means of said label wherein any DNA-BP complexes detected are indicative of the presence of DNA in said sample.

6. A method according to claim 5, wherein said photoreactive compound is isopsoralen.

7. A method according to claim 6, wherein said detectable label is biotin.

8. A method according to claim 7, wherein said biotin is detected using a conjugate comprising avidin, streptavidin or antibiotin joined to an enzyme, radioisotope or fluorophore.

9. A method according to any one of claims 1, 3, or 5, wherein said BP is single-stranded DNA binding protein, $T^4$ gene 32 protein or topoisomerase I.

10. A method according to any one of claims 1, 3, or 5, wherein said label is an enzyme joined to said BP.

11. A method according to claim 10, wherein said enzyme is urease or horseradish peroxidase.

12. A method according any one of claims 1, 3, or 5, further comprising:
    additionally treating at least one background solution containing no DNA and at least one reference solution containing a known amount of DNA according to the steps of any one of claims 1, 3, or 5;
    subtracting the label bound in said background solution from any DNA-BP complexes detected for said sample and from the label detected in said reference solution to produce an adjusted signal for said sample and for said reference solution; and relating the adjusted signals for said sample and said reference solution to determine the amount of DNA present in said sample.

13. A method according to any one of claims 1, 3, or 5, wherein said sample further comprises protein.

14. A method according to claim 13, wherein said protein-containing sample is deproteinized prior to said contacting.

15. A method according to claim 14, wherein said protein-containing sample is deproteinized by a method comprising:

admixing said protein-containing sample with (a) a suspension comprising glass particles and (b) sufficient iodide to cause any DNA in said protein-containing sample to bind to said glass particles;

isolating said glass particles; and eluting any DNA from said particles.

16. A method according to claim 15, wherein said eluting is carried out with water or phosphate buffered saline.

17. A method according to claim 14, wherein said protein-containing sample is deproteinized by a method comprising:

admixing said protein-containing sample with a proteolytic anzyme composition under conditions whereby protein present is hydrolyzed.

18. A method according to claim 17, further comprising:

after said admixing, separating any product of said hydrolyzed protein from any DNA.

19. A method according to claim 18, wherein said separating comprises:

after said admixing, centrifuging said sample through a membrane with a low molecular weight cutoff or passing said sample through an ultrafiltration device with a low molecular weight cutoff; and recovering any DNA present.

20. A method according to claim 17, wherein said proteolytic enzyme composition comprises at least one of pronase or proteinase K.

21. A method according to claim 5, wherein said detectable label is a radionuclide or biotin.

22. A method according to claim 5, wherein said mixture is subjected to DNA denaturing conditions prior to said contacting.

23. A method according to claims 1, 3, or 5, wherein the high affinity single-stranded DNA binding protein has an affinity for single-stranded DNA of at least about $10^5 M^{-1}$.

24. A method according to any one of claims 1, 3, or 5, wherein the high affinity single-stranded DNA binding protein has an affinity for single-stranded DNA of about $10^8$ to about $10^{10} M^{-1}$.

25. A method according to claim 24, wherein the single-stranded DNA has at least 100 nucleotides.

26. A method according to any one of claims 1, 3, or 5, wherein the high affinity single-stranded DNA binding protein has a single-stranded DNA binding affinity such that the high affinity single-stranded DNA binding protein may be eluted from single-stranded DNA-cellulose or single-stranded DNA-Sepharose by a sodium chloride concentration of greater than about 0.4M.

27. A method according to any one of claims 1, 3, or 5, wherein the high affinity single-stranded DNA binding protein has a single-stranded DNA binding affinity such that the high affinity single-stranded DNA binding protein may be eluted from single-stranded DNA-cellulose or single-stranded DNA-Sepharose by a sodium chloride concentration of greater than about 0.6M.

* * * * *